United States Patent
Takenaka et al.

(10) Patent No.: US 10,105,680 B2
(45) Date of Patent: Oct. 23, 2018

(54) ACTIVATED CARBON WITH EXCELLENT ADSORPTION PERFORMANCE AND PROCESS FOR PRODUCING SAME

(71) Applicant: KANSAI COKE AND CHEMICALS CO., LTD., Hyogo (JP)

(72) Inventors: Shoichi Takenaka, Hyogo (JP); Kojiro Tenno, Hyogo (JP)

(73) Assignee: KANSAI COKE AND CHEMICALS CO., LTD., Hyogo (JP)

( * ) Notice: Subject to any disclaimer, the term of this patent is extended or adjusted under 35 U.S.C. 154(b) by 0 days.

(21) Appl. No.: 15/329,054

(22) PCT Filed: Jul. 23, 2015

(86) PCT No.: PCT/JP2015/070979
§ 371 (c)(1),
(2) Date: Jan. 25, 2017

(87) PCT Pub. No.: WO2016/013619
PCT Pub. Date: Jan. 28, 2016

(65) Prior Publication Data
US 2017/0209848 A1   Jul. 27, 2017

(30) Foreign Application Priority Data

Jul. 25, 2014   (JP) .................................. 2014-152010

(51) Int. Cl.
| | | |
|---|---|---|
| B01J 20/20 | (2006.01) | |
| B01J 20/30 | (2006.01) | |
| B01J 20/28 | (2006.01) | |
| B82Y 40/00 | (2011.01) | |
| C01B 32/342 | (2017.01) | |
| B82Y 30/00 | (2011.01) | |
| C07C 17/389 | (2006.01) | |
| C01B 32/348 | (2017.01) | |

(52) U.S. Cl.
CPC .............. B01J 20/20 (2013.01); B01J 20/28 (2013.01); B01J 20/28071 (2013.01); B01J 20/28083 (2013.01); B01J 20/30 (2013.01); B01J 20/3064 (2013.01); B01J 20/3078 (2013.01); B82Y 30/00 (2013.01); B82Y 40/00 (2013.01); C01B 32/342 (2017.08); C01B 32/348 (2017.08); C07C 17/389 (2013.01); C01P 2006/14 (2013.01); C01P 2006/16 (2013.01)

(58) Field of Classification Search
CPC ............... B01D 53/02; B01D 53/261; B01D 2253/102; B01D 2253/306; B01J 20/20; B01J 20/28023; B01J 20/28057; B01J 20/28059; B01J 20/28061
See application file for complete search history.

(56) References Cited

U.S. PATENT DOCUMENTS

| | | | | |
|---|---|---|---|---|
| 4,737,889 A | * | 4/1988 | Nishino | ................. H01G 9/155 162/138 |
| 5,880,061 A | | 3/1999 | Yoshino et al. | |
| 2009/0038632 A1 | | 2/2009 | Cashmore et al. | |
| 2014/0231342 A1 | | 8/2014 | Yamanoi et al. | |

FOREIGN PATENT DOCUMENTS

| | | |
|---|---|---|
| JP | 60-34674 | 2/1985 |
| JP | 61-242909 | 10/1986 |
| JP | 5-302216 | 11/1993 |
| JP | 6-198165 | 7/1994 |
| JP | 8-24636 | 1/1996 |
| JP | 8-281099 | 10/1996 |
| JP | 8-337412 | 12/1996 |
| JP | 9-155187 | 6/1997 |
| JP | 10-70049 | 3/1998 |
| JP | 11-240707 | 9/1999 |
| JP | 11-307406 | 11/1999 |
| JP | 2003-104710 | 4/2003 |
| JP | 2003-178761 | 6/2003 |
| JP | 2004-182511 | 7/2004 |
| JP | 2004-182568 | 7/2004 |
| JP | 2006-326405 | 12/2006 |
| JP | 2008-100186 | 5/2008 |
| JP | 2008-149267 | 7/2008 |
| JP | 2008-535754 | 9/2008 |
| JP | 2011-46584 | 3/2011 |
| JP | 2013-220413 | 10/2013 |
| WO | 2012/108198 | 8/2012 |

OTHER PUBLICATIONS

Foster et al., Adsorption Characteristics of Trace Volatile Organic Compounds in Gas Streams onto activated carbon Fibers (Chem. Mater. 1992, 4, 1068-1073).*
Notification of Reasons for Rejection dated Oct. 27, 2015 in Japanese Application No. 2014-152010, with Full English Translation.
Written Opposition of the Grant of a Patent issued Sep. 14, 2016 in Japanese Patent No. 5886383, with Partial English Translation.
Web page of Customer Affairs Agency, House Hold Goods Quality Labeling Act, water purifiers, with Partial English Translation & cited in CB, http://www.caa.go.jp/hinpyo/guide/zakka/zakka_34.html, printed Sep. 2, 2016, 7 pgs.
Web page of Tokyo Water Authority, Water quality management goal setting items, water source and water quality, with Partial English Translation & cited in CB, http:/www.waterworks.metro.tokyo.jp/suigen/kijun/s_kijun2.html, printed Sep. 2, 2016, 5 pgs.

(Continued)

*Primary Examiner* — Jafar F Parsa
(74) *Attorney, Agent, or Firm* — Wenderoth, Lind & Ponack, L.L.P.

(57) ABSTRACT

The object of the present invention is to provide an activated carbon with a large equilibrium adsorption amount of 1,1,1-trichloroethane. And the activated carbon of the invention comprising: an equilibrium adsorption amount of 1,1,1-trichloroethane is 20 mg/g or more and a pore volume with the pore diameters of more than 20 Å and 300 Å or less is 0.04 cm$^3$/g or more.

5 Claims, 10 Drawing Sheets

(56) References Cited

OTHER PUBLICATIONS

Web page of Ministry of Health, Labour and Welfare, 1,1,1-trichloroethane, with Partial English Translation & cited in CB, 5 pgs.
Yoshida, "Handbook on Porous Adsorbents", Fuji Technosystem, 1st edition, $1^{st}$ copy, pp. 672-675 (2005), with Partial Translation & cited in CB.
Sakakura, Japanese Standards Association, Japan Industrial Standard, "Testing methods for house hold water purifiers", JIS S 3201 (2004), with Partial English Translation & cited in CB, 10 pgs.
Takeuchi, "Latest adsorption technology hand book—process, material, design", 1st edition, pp. 575-576 (1999), with Partial English Translation & cited in CB.
Written Opinion dated Oct. 13, 2015 in corresponding International Application No. PCT/JP2015/070979, with English Translation & cited in CB.
Tai et al., "Activated Carbon Fiber Special", Activated Carbon Fiber, SEN-I-GAKKAISHI (Fiber and Industrialization), vol. 49, No. 5, pp. 177-182 (1993), with Partial English Translation & cited in CB.
Yoshida, "Handbook on Porous Adsorbents", Fuji Technosystem, 1st edition, 1st copy, pp. 91-93 (2005), with Partial English Translation & cited in CB.
Shimazaki, "Change in adsorption ability and pores along with an activation of polyacrylonitrile-base activated carbon fiber", The Journal of the Chemical Society of Japan, vol. 1, pp. 54-61 (1993), with Partial English Translation & cited in CB.
Second Written Opposition of the Grant of a Patent issued Sep. 16, 2016 in Japanese Patent No. 5886383, with Partial English Translation.
"Company brochure company's outline", web page of Kuraray Chemical Co., Ltd., with Partial Translation added in postscript & cited in CM, http://www.kuraray-c.co.jp/company/index.html, printed Sep. 5, 2016, 3 pgs.
Kuraray Chemical Co., Ltd., product listing web page, (2016), cited in CM, http://www.kuraraychemical.com/index.html, printed Sep. 5, 2016, 1 pg.
Notification of Reasons for Revocation dated Jun. 20, 2017 in Japanese Patent No. 5886383, with Partial English Translation.
Tatsumoto et al., "Applied Technology of Activated Carbon", Technosystem Co., Ltd., 1st Edition, 1st Issue, pp. 65-72, Jul. 25, 2000, with Partial English Translation.
Kuraray Chemical Co., Ltd., Kuraray Carbon Product Selection Recommendation and Kuraray Products Application Summary Chart, (2016), cited in CM, http://www.kuraraychemical.com/Products/Products.htm, printed Sep. 5, 2016, 3 pgs.
Kuraray Chemical Co., Ltd., "Kuractive Technical Report", Jul. 12, 2002, 2 pgs., cited in CM.
Kuraray Chemical Co., Ltd., "Activated Carbon Fiber Kuractive", Oct. 30, 2002, 7 pgs., cited in CM.
Kuraray Chemical Co., Ltd., "Kuractive Technical Report, The Performance Carbon" cited in CM, http://www.kuraraychemical.com/Technical/Kuraactive/Kuraactive.htm, printed Sep. 5, 2016, 1 pg.
Kuraray Chemical Co., Ltd., "Activated Carbon Fiber Kuractive" (2002), 7 pgs., cited in CM.
Kuraray Chemical Co., Ltd., "Kuractive Technical Report, The Performance Carbon" (2012), 1 pg., cited in CM.
Kuraray Chemical Co., Ltd., "Activated Carbon Fiber Kuractive" (2012), 7 pgs., cited in CM.
Kuraray Chemical Co., Ltd., "Kuractive Technical Report, The Performance Carbon" (2015), 2 pgs., cited in CM.
Kuraray Chemical Co., Ltd., "Activated Carbon Fiber Kuractive" (2015), 7 pgs., cited in CM.
Kuraray Chemical Co., Ltd., "Activated Carbon Analysis Report", prepared by Kuraray Chemical Co., Ltd., Jul. 7, 2014, 1 pg., cited in CM.
Kuraray Chemical Co., Ltd., "Activated Carbon Analysis Report", prepared by Kuraray Chemical Co., Ltd., Nov. 13, 2014, 1 pg., cited in CM.
MC Evolve Technologies Corporation "Analysis Report", prepared by MC Evolve Technologies Corporation, Sep. 14, 2016, with Partial English Translation & cited in CM, 8 pgs.
Shimadzu Techno-Research, Inc., "Analysis Report", prepared by Shimadzu Techno-Research, Inc., Sep. 15, 2016, 41 pgs., with Partial English Translation & cited in Cm.
Shimadzu Corporation, "Total pore volume of average pore diameter by gas adsorption process", practical course: easy powder course by a powder doctor, printed Sep. 8, 2016, 2 pgs., with Partial English Translation & cited in CM http://www.an.shimadzu.co.jp/powder/lecture/practice/p02/lesson14.htm.
Sumika Chemical Analysis Service, Ltd., "Physical properties of powders", Analytical technique information magazine (SCAS News), vol. 14 (2001), 8 pgs., with Partial English Translation & cited in CM, https://www.scas.co.jp/scas_news/news/2001_2_vol14.html.
Notification of Reasons for Revocation dated Jan. 4, 2017 in Japanese Patent No. 5886383, with Full English Translation, 11 pgs.
International Search Report dated Oct. 13, 2015 in corresponding International Application No. PCT/JP2015/070979.
Chinese Office Action dated Mar. 28, 2018 in corresponding Chinese Patent Application No. 201580041107.3 with English Translation.
Notice of Reasons for Revocation dated Dec. 20, 2017 in Japanese Patent No. 5886383, with partial English translation.

\* cited by examiner

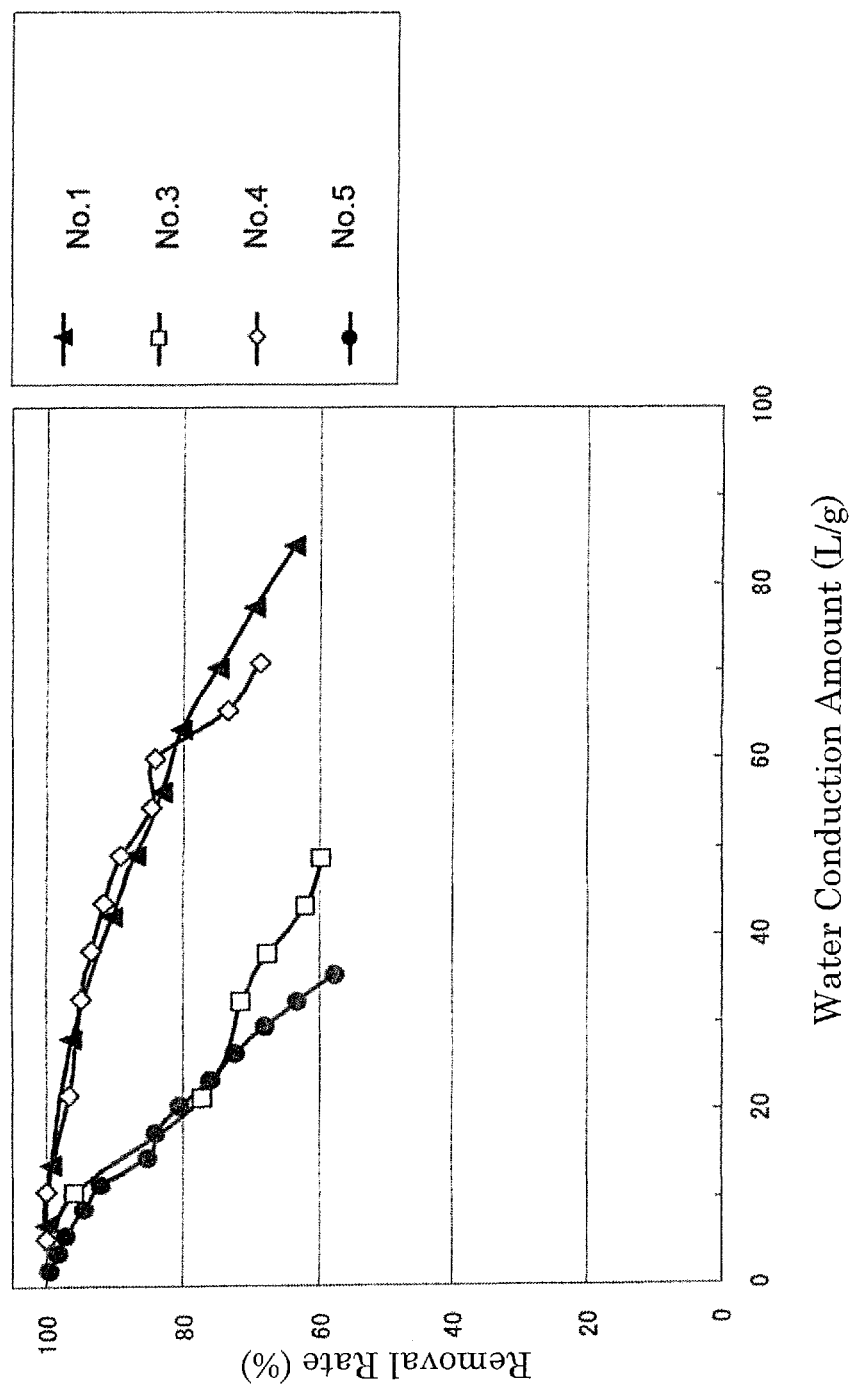
[Fig. 1]

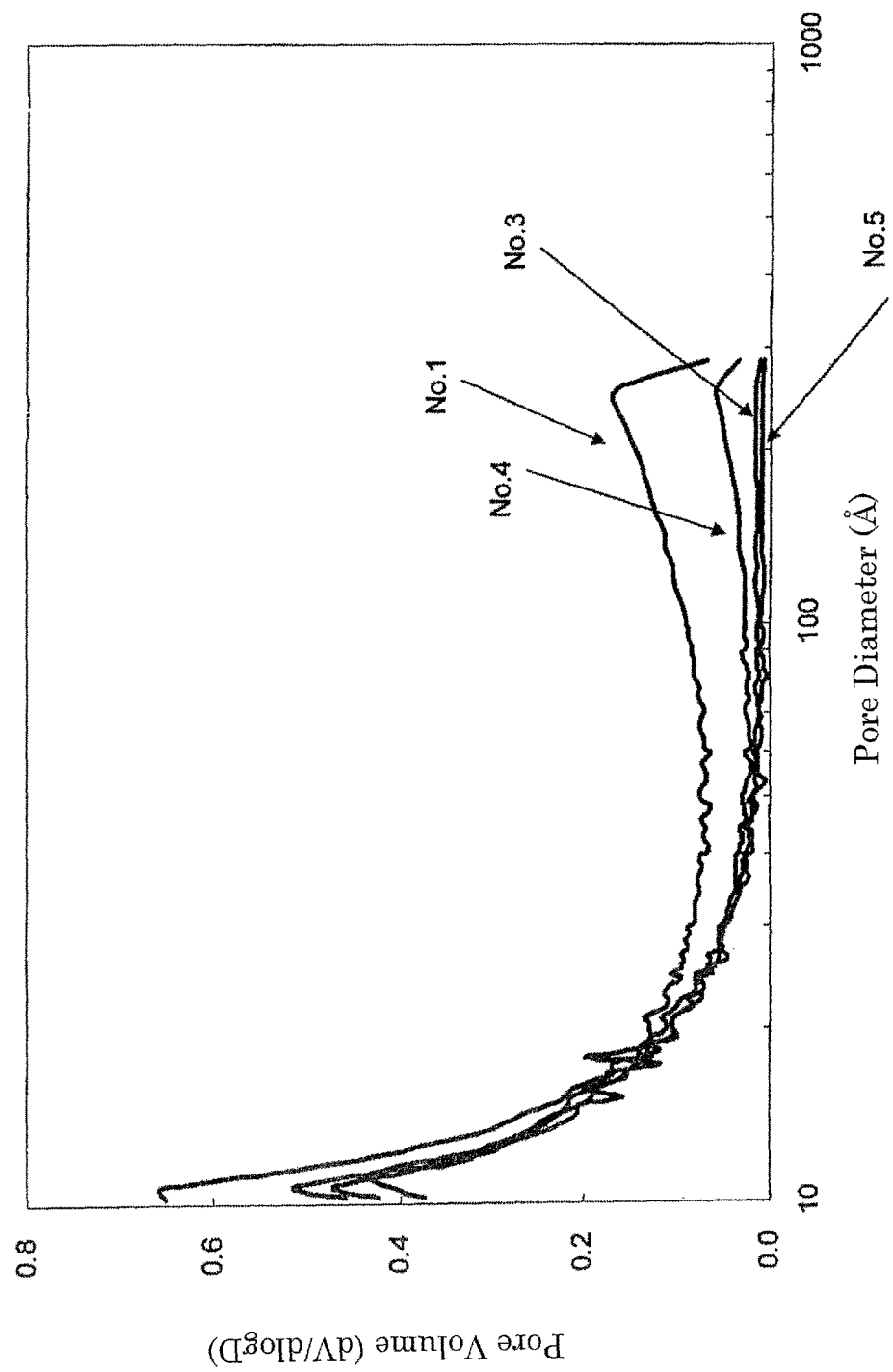
[Fig. 2]

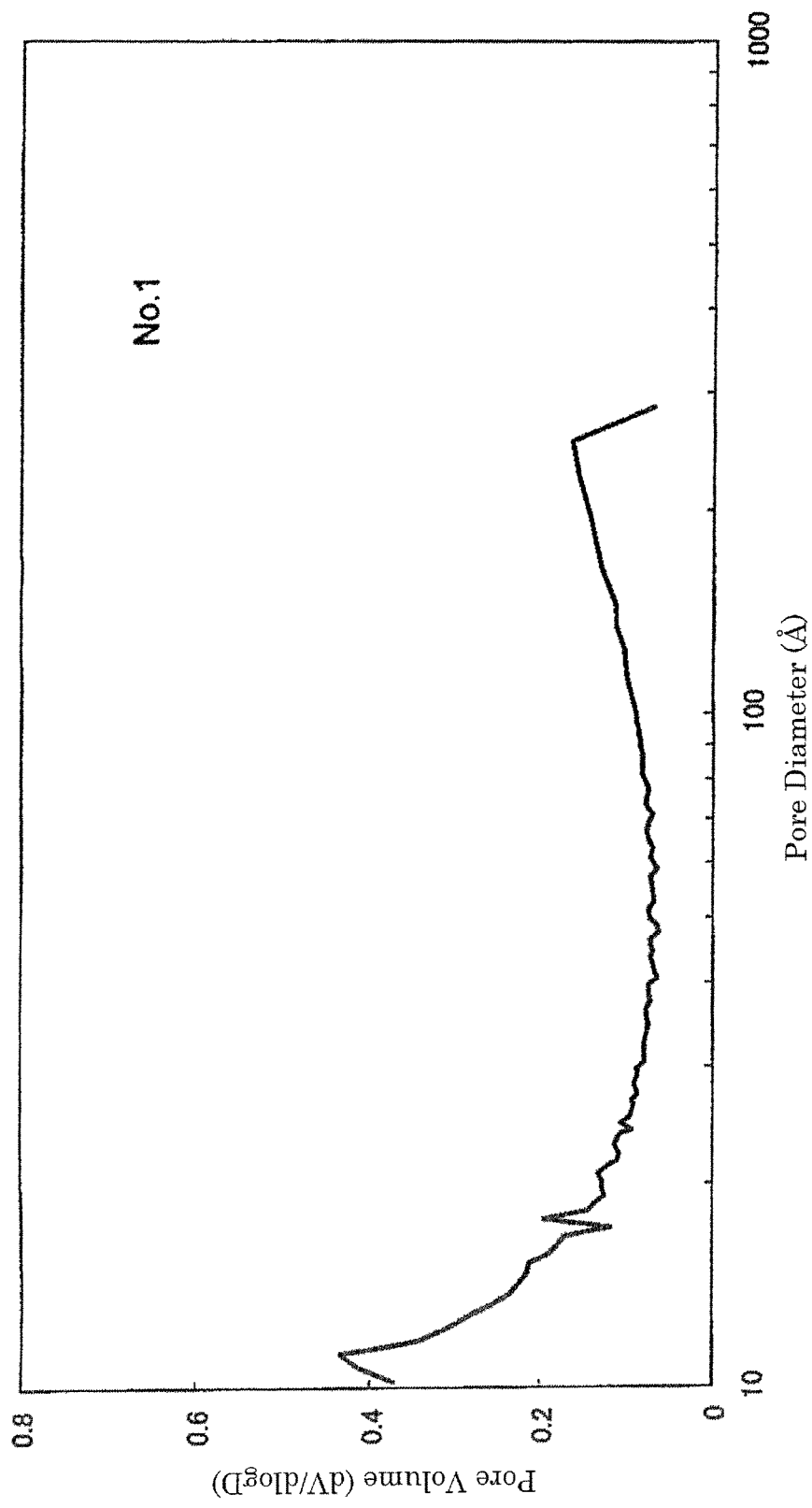
[Fig. 3]

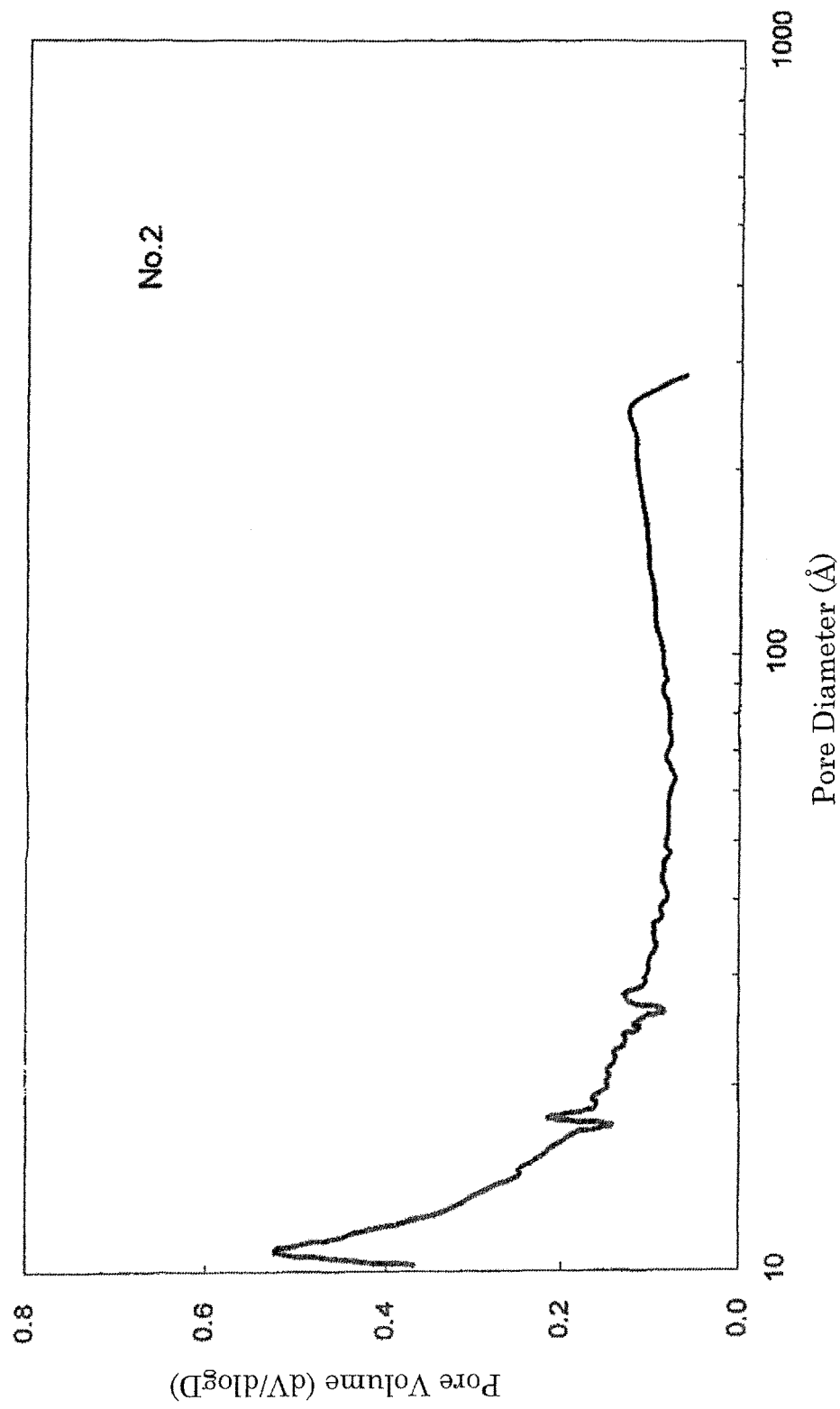
[Fig. 4]

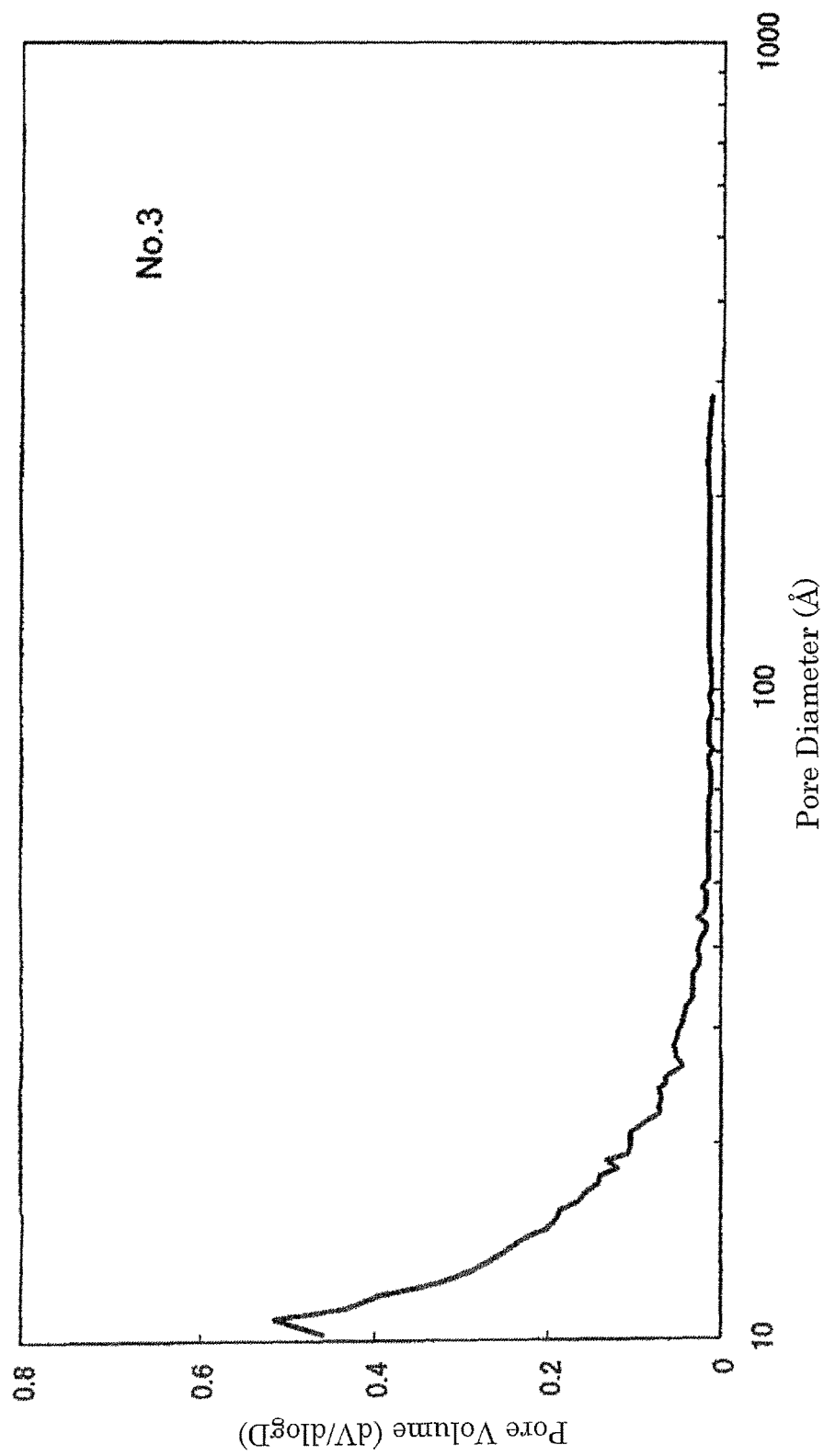
[Fig. 5]

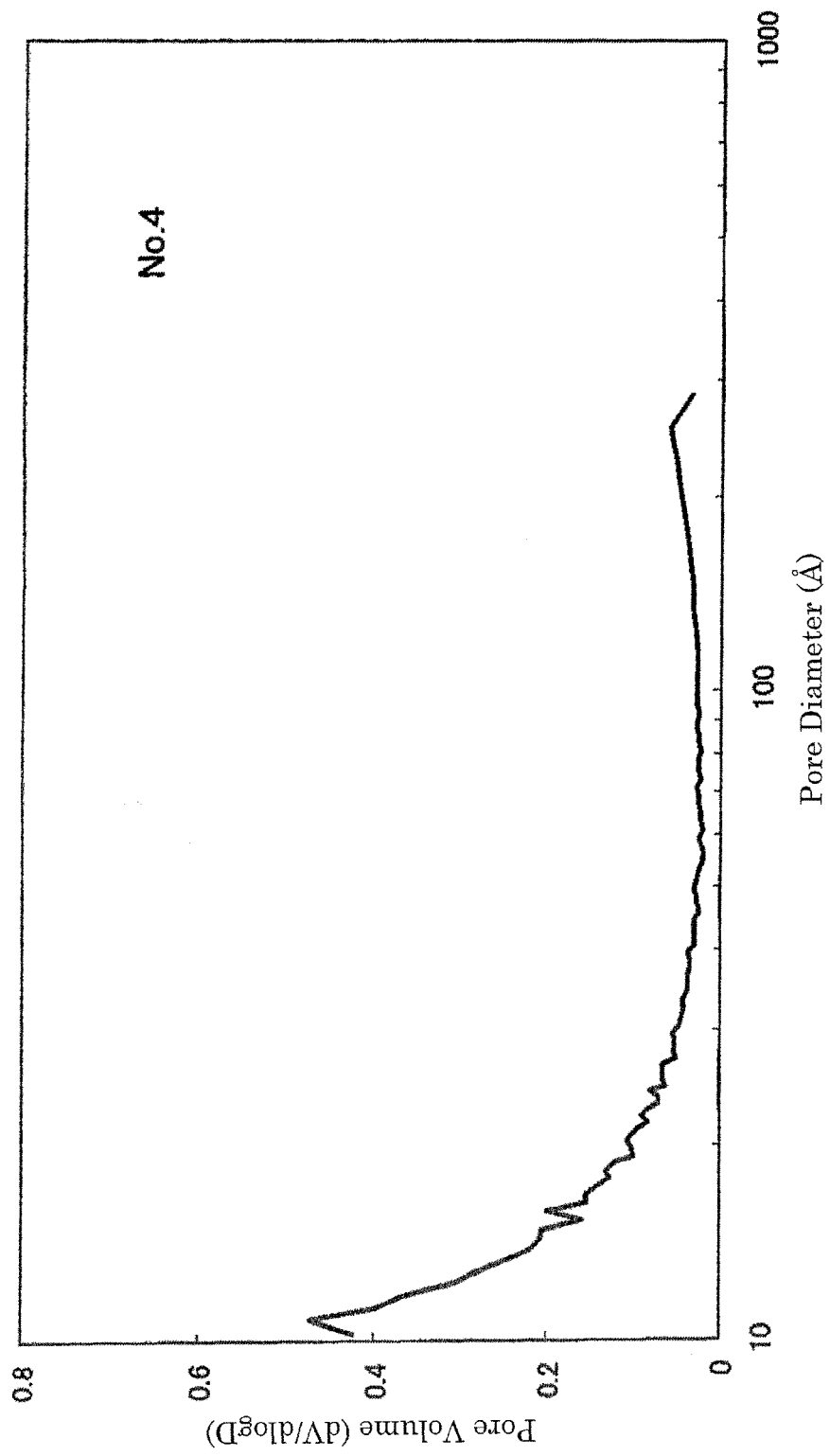
[Fig. 6]

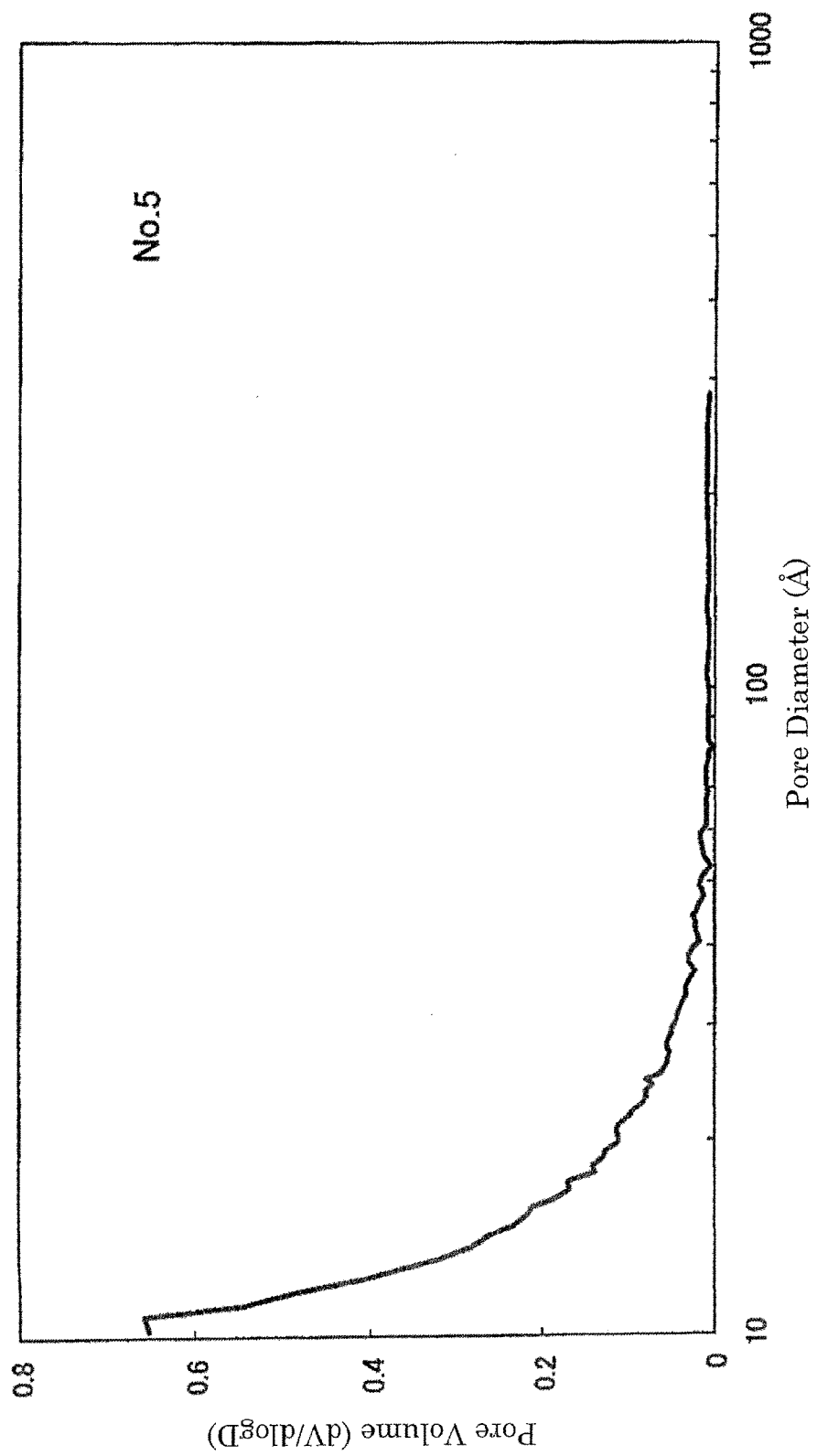
[Fig. 7]

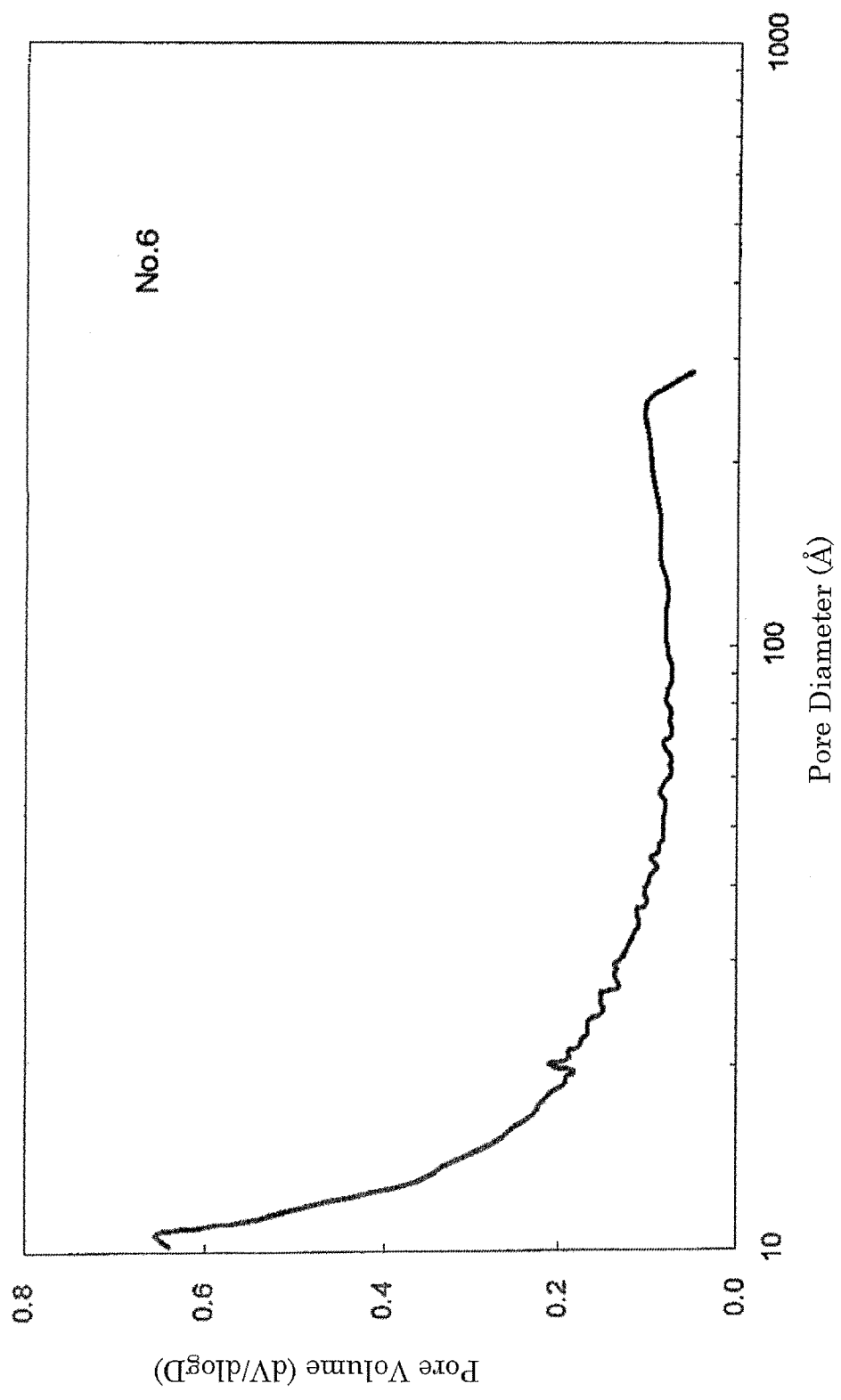
[Fig. 8]

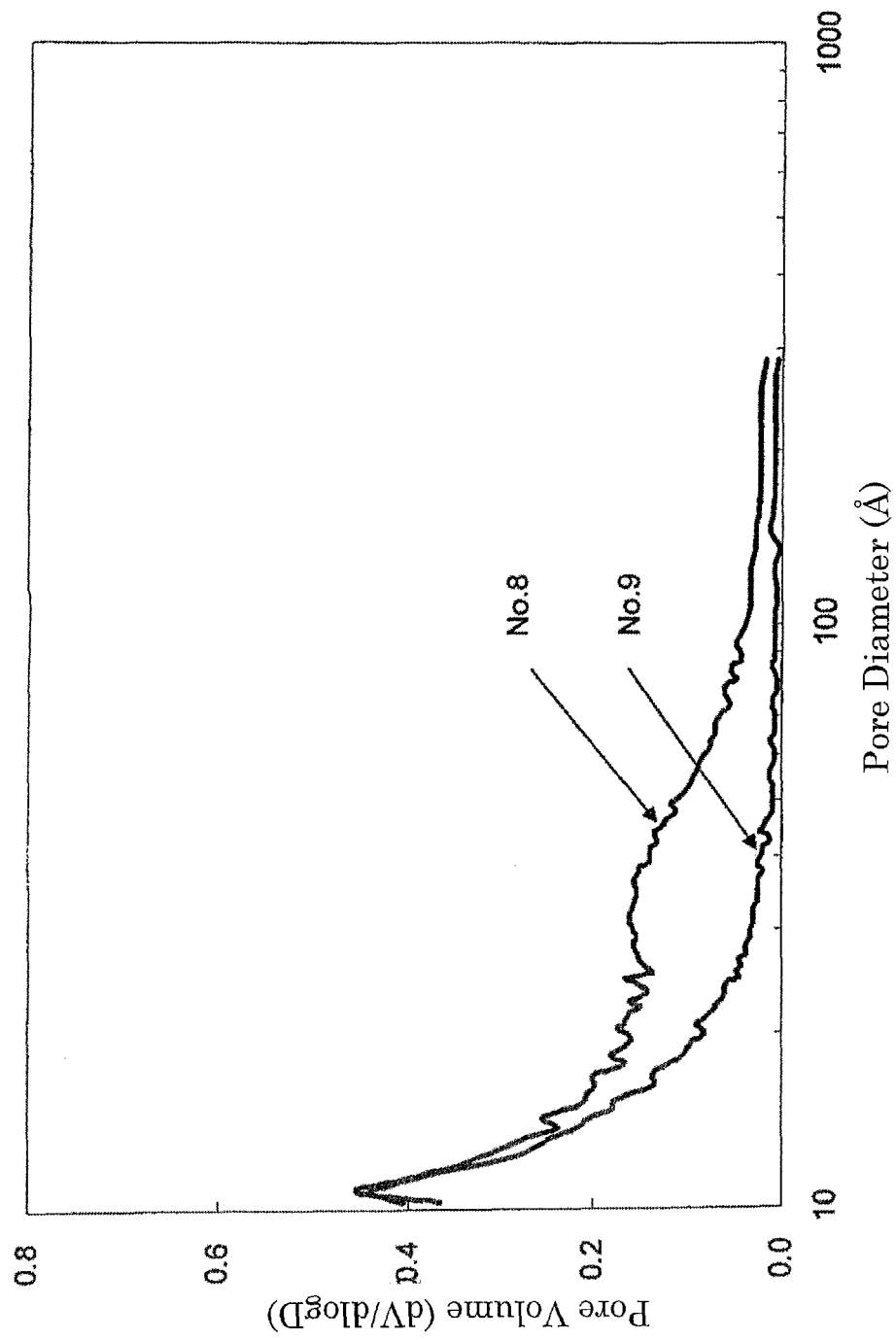
[Fig. 9]

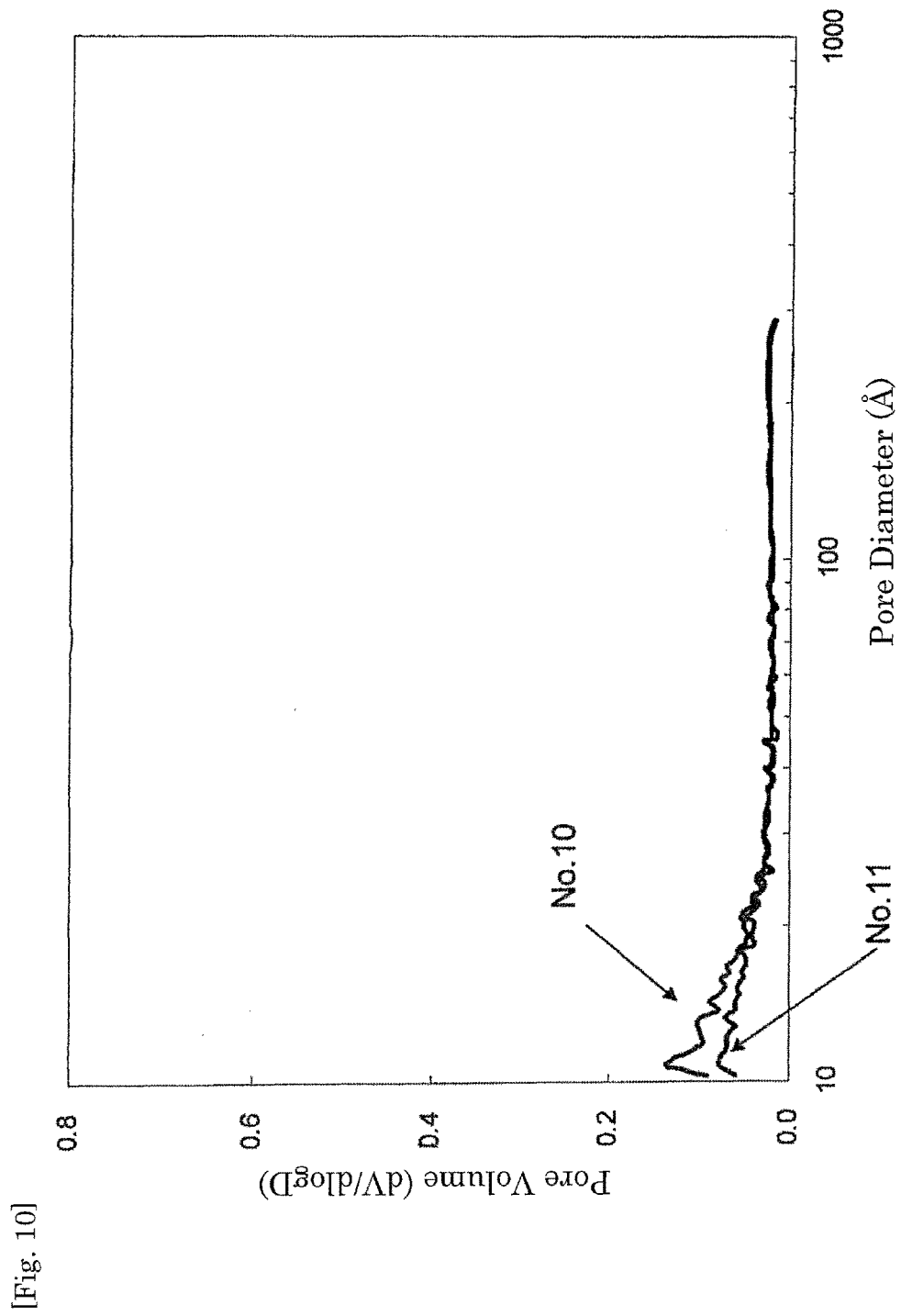
[Fig. 10]

ACTIVATED CARBON WITH EXCELLENT ADSORPTION PERFORMANCE AND PROCESS FOR PRODUCING SAME

TECHNICAL FIELD

The present invention relates to an activated carbon with excellent adsorption performance and process for producing same.

BACKGROUND ART

Since it is obligation to treat raw water for tap water by chlorination, the tap water after the treatment contains a certain amount of residual chlorine. Whereas, such residual chlorine has, beside a bactericidal action, an effect of oxidative decomposition of organic matters and generates organic halogen compounds such as trihalomethanes that are carcinogens. Such organic halogen compounds remaining in tap water have small molecular weights, and concentrations thereof in the tap water are very low. Thus, it has been difficult for conventional activated carbon to remove these organic halogen compounds sufficiently.

In order to solve this problem, optimization of pore diameter distribution of the activated carbon has been proposed. Conventionally, it has been thought that increase of a mesopore volume ratio is effective for the adsorption of such organic halogen compounds, so that various proposals have been offered.

For example, as activated carbon that is suitable for removing musty odor and trihalomethane, Patent Document 1 discloses activated carbon, of which a specific surface area of pores having diameters of 20 Å or more is 30 $m^2/g$ or more and 2500 $m^2/g$ or less, and a specific surface area of pores having diameters of less than 20 Å is 600 $m^2/g$ or more and 2500 $m^2/g$ or less. Also, as a method for manufacturing such activated carbon, a method including: mixing an organometallic compound such as a yttrium compound, a titanium compound and a zirconium compound with an activated carbon precursor in solvent; and performing carbonization treatment and activation treatment to the obtained mixture is disclosed.

Moreover, Patent Document 2 discloses a method for manufacturing activated carbon which adsorbs and removes trihalomethane precursors having comparatively high molecular weights (molasses and the like), and specifically discloses a method for modifying carbonaceous fiber, which includes: performing hydrophilic treatment to the carbonaceous fiber having a specific surface area of 0.1 $m^2/g$ to 1200 $m^2/g$ with an oxidant; and subsequently allowing the carbonaceous fiber to support alkali earth metal so as to perform activation treatment.

Furthermore, it has been thought that, in order to improve adsorption performance of activated carbon in dynamic adsorption under a water conducting condition, increase in contact efficiency between an adsorbate and micropores is effective. As a means for increasing the contact efficiency, various techniques for controlling mesopores which serve as introduction pores into the micropores have been proposed.

For example, Patent Document 3 discloses an organic halogen compound-removing filter, which is obtained by performing heat treatment to a mixture of; fibrous activated carbon of which a specific surface area of mesopores having pore diameters of 20 Å or more and less than 500 Å ranges from 100 $m^2/g$ to 2500 $m^2/g$, a specific surface area of micropores having pore diameters of less than 20 Å ranges from 600 $m^2/g$ to 2500 $m^2/g$, and a ratio of a mesopore volume with respect to a total pore volume ranges from 10% to 40%; and heat-fusible fiber, the organic halogen compound-removing filter being made of a molded body having apparent density of 0.25 $g/cm^3$ to 0.60 $g/cm^3$. Further, as a method for controlling the specific surface area, a manufacturing method including; mixing an organometallic compound (a yttrium compound, a titanium compound, a zirconium compound or the like) with an activated carbon precursor; and thereafter performing spinning fiber, infusibilization treatment, carbonization treatment and activation treatment is disclosed.

Moreover, Patent Document 4 discloses activated carbon, of which a mesopore volume in a range of pore diameters of 30 Å or more and less than 50 Å in pore diameter distribution that is obtained by a BJH method from a nitrogen adsorption isothermal line at 77.4 K ranges from 0.02 cc/g to 0.40 cc/g, and a ratio of the mesopore volume in the range with respect to a total pore volume ranges from 5% to 45%. As a method for controlling the pore volume, Patent Document 4 discloses a method for manufacturing activated carbon, in which a pitch containing 0.01% to 5% by weight of at least one kind of a metal component among Mg, Mn, Fe, Y, Pt and Gd is used as an activated carbon precursor, and the precursor is subjected to infusibilization treatment or carbonization treatment and activation treatment, wherein a mesopore mode diameter of the obtained activated carbon is controlled by varying the kind of the metal component.

PRIOR ART DOCUMENTS

Patent Documents

Patent Document 1: JP-A-11-240707
Patent Document 2: JP-A-5-302216
Patent Document 3: JP-A-2008-149267
Patent Document 4: JP-A-2004-182511

SUMMARY OF THE INVENTION

Problems to be Solved by the Invention

There has been a problem that it is difficult for a conventionally proposed activated carbon to remove 1,1,1-trichloroethane among trihalo compounds, and in particular, dynamic adsorption under a water conducting condition can hardly remove 1,1,1-trichloroethane.

The present invention has been made in the light of the problems described above, the object of the present invention is to provide: activated carbon, which not only has a large equilibrium adsorption amount of 1,1,1-trichloroethane but also exhibits excellent adsorption performance of 1,1,1-trichloroethane even under the water conducting condition; and a method for manufacturing the same.

Solutions to the Problems

An activated carbon of the present invention which can solve the above problems is an activated carbon comprising an equilibrium adsorption amount of 1,1,1-trichloroethane is 20 mg/g or more and a pore volume with the pore diameters of more than 20 Å and 300 Å or less is 0.04 $cm^3/g$ or more.

The activated carbon of the present invention is preferably have a pore volume with the pore diameters of more than 200 Å and 300 Å or less is 0.01 $cm^3/g$ or more. And the activated carbon preferably has a peak higher than that of a log differential pore volume value with the pore diameter of 100 Å in a range of the pore diameters of more than 200 Å and 300 Å or less in a pore diameter distribution diagram (vertical axis: log differential pore volume dV/d log D (cm³/g), horizontal axis: pore diameter D (Å)) obtained by measurement by a nitrogen adsorption method.

A method for producing above activated carbon of the present invention is treating a phenol resin derivative sequentially by carbonizing a phenol resin fiber, and subsequently activating the phenol resin fiber carbide at least once, wherein any one of the activation is a steam activation, and loading the phenol resin derivative with at least one of a calcium compound or a potassium compound by the time when performing the one-time steam activation, and conducting the one-time steam activation of thus obtained loaded phenol resin derivative while maintaining the loading state.

In the production method of the above activated carbon of the present invention, it is preferable that (1) the phenol resin fiber is loaded with at least one of the calcium compound or the potassium compound, and subsequently carbonizing the loaded phenol resin fiber, and then conducting the steam activation of the obtained loaded carbide; or (2) the phenol resin fiber is carbonized, and subsequently loading the phenol resin fiber carbide with at least one of the calcium compound or the potassium compound, and then conducting the steam activation of the obtained loaded carbide; or (3) the phenol resin fiber is carbonized and subsequently activated, and thus obtained activated phenol resin fiber is loaded with at least one of a calcium compound or a potassium compound, and then, conducting the steam activation of the loaded phenol resin.

Effect of the Invention

The activated carbon of the present invention can exhibit not only the superior equilibrium adsorption amount of 1,1,1-trichloroethane but also the excellent adsorption performance even under the water conducting condition because of its optimized pore structure. And the above activated carbon of the present invention can be easily produced by the production method of the present invention.

BRIEF DESCRIPTION OF THE DRAWINGS

FIG. 1 is a graph showing relation between the water conduction amount and a removal rate of 1,1,1-trichloroethane of Water Conduction Test of Activated Carbon Nos. 1, 3, 4 and 5 of EXAMPLES.

FIG. 2 is a graph showing pore diameter distribution of Activated Carbon Nos. 1, 3, 4 and 5 of EXAMPLES.

FIG. 3 is a graph showing pore diameter distribution of Activated Carbon No. 1 of EXAMPLES.

FIG. 4 is a graph showing pore diameter distribution of Activated Carbon No. 2 of EXAMPLES.

FIG. 5 is a graph showing pore diameter distribution of Activated Carbon No. 3 of EXAMPLES.

FIG. 6 is a graph showing pore diameter distribution of Activated Carbon No. 4 of EXAMPLES.

FIG. 7 is a graph showing pore diameter distribution of Activated Carbon No. 5 of EXAMPLES.

FIG. 8 is a graph showing pore diameter distribution of Activated Carbon No. 6 of EXAMPLES.

FIG. 9 is a graph showing pore diameter distribution of Activated Carbon Nos. 8 and 9 of EXAMPLES.

FIG. 10 is a graph showing pore diameter distribution of Activated Carbon Nos. 10 and 11 of EXAMPLES.

MODE FOR CARRYING OUT THE INVENTION

An organic halogen compound having a small number of carbons such as trihalomethane is known to be adsorbed by micropores of 20 Å or less because of its small molecular size. However, 1,1,1-trichloroethane has a molecular size that is larger than trihalomethanes by one carbon, and because of this slight difference, the conventional activated carbon, which even has a sufficient volume of the micropores, has exhibited less adsorption performance of 1,1,1-trichloroethane. In particular, activated carbon having excellent adsorption performance of 1,1,1-trichloroethane under a water conducting condition has not been proposed yet.

Then, the inventors of the present invention have examined activated carbon which not only has a large equilibrium adsorption amount of 1,1,1-trichloroethane but also exhibits excellent adsorption performance even under the water conducting condition. More specifically, they have considered that, although the molecular size of 1,1,1-trichloroethane is larger by one carbon, it is sufficiently smaller than the micropores, whereby its characteristic of being adsorbed by the micropores should not be not changed. They have inferred that the equilibrium adsorption amount of 1,1,1-trichloroethane is lacked compared with the volume of the micropores under such a situation, because of insufficient development of the mesopores having pore diameters of from more than 20 Å to 500 Å or less, which serve as introduction paths into the micropores. However, if the mesopores are developed, such development causes erosion of the micropores, whereby the volume of the micropores is generally decreased. Under such a situation, the inventors of the present invention have found that the mesopores can be developed while maintaining the pore volume of the micropores sufficiently, so that the use of such activated carbon can realize a sufficient adsorption amount and in-pore diffusion of 1,1,1-trichloroethane in good balance, whereby such activated carbon can consequently exhibit excellent adsorption performance of 1,1,1-trichloroethane.

The activated carbon of the present invention strictly controls: the pore volume of the micropores contributing to the improvement of the adsorption amount of 1,1,1-trichloroethane; and a pore volume of mesopores having pore diameters of more than 20 Å to 300 Å or less (hereinafter, also called as the "pore volume with the pore diameters of 20 Å to 300 Å") among mesopores that contribute to the improvement of a diffusion rate of 1,1,1-trichloroethane, whereby the equilibrium adsorption amount of 1,1,1-trichloroethane and the adsorption performance thereof under the water conducting condition, that is, a water conduction amount can be improved.

1,1,1-trichloroethane is adsorbed by the micropores, and it is desirable that, for increasing the adsorption amount of 1,1,1-trichloroethane, many of the micropores have suitable pore diameters for the molecular size of 1,1,1-trichloroethane. In the present invention, as an index for such a suitable pore diameter for adsorbing 1,1,1-trichloroethane, the equilibrium adsorption amount is used. As a sufficient adsorption amount of 1,1,1-trichloroethane, the equilibrium adsorption amount of 1,1,1-trichloroethane in equilibrium tests of the examples is at least 20 mg/g or more, preferably 25 mg/g or more, more preferably 30 mg/g or more, and further preferably 35 mg/g or more. The larger equilibrium adsorption amount is more preferable, because the adsorption amount is improved, and its upper limit is not determined.

Further, the pore volume with the pore diameters of 20 Å to 300 Å of the activated carbon of the present invention is 0.04 cm³/g or more. If increasing the pore volume with the pore diameters of 20 Å to 300 Å, contact efficiency between 1,1,1-trichloroethane and the micropores can be improved under the water conducting condition. The pore volume with the pore diameters of 20 Å to 300 Å is 0.04 cm³/g or more, is preferably 0.05 cm³/g or more, and is further preferably 0.10 cm³/g or more, which is larger the better.

On the other hand, the pore volume with the pore diameters of 20 Å to 300 Å is too large, density of the activated carbon becomes low, so that a limited space cannot be sometimes filled with a required amount of the activated carbon. Thus, the pore volume with the pore diameters of 20 Å to 300 Å is preferably 2.0 cm³/g or less, and more preferably 1.0 cm³/g or less.

According to the activated carbon of the present invention satisfying the above-determined equilibrium adsorption amount and the above-determined pore volume with the pore diameters, 1,1,1-trichloroethane can be diffused and move quickly in the activated carbon, and an adsorption site can be utilized efficiently. As a result, the water conduction amount is increased, so that the excellent adsorption performance of 1,1,1-trichloroethane can be exhibited under the water conducting condition.

Hereinafter, preferable structures of the activated carbon of the present invention will be described.

In the activated carbon of the present invention, the pore volume with the pore diameters of 20 Å to 300 Å is appropriately controlled as described above, and it is desirable that preferably the pore volume with the pore diameters of more than 50 Å and 300 Å or less (hereinafter, also called as the "pore volume with the pore diameters of 50 Å to 300 Å") be controlled, more preferably the pore volume with the pore diameters of more than 100 Å and 300 Å or less (hereinafter, also called as the "pore volume with the pore diameters of 100 Å to 300 Å") be controlled, and further preferably the pore volume with the pore diameters of more than 200 Å and 300 Å or less (hereinafter, also called as the "pore volume with the pore diameters of 200 Å to 300 Å") be appropriately controlled. By controlling the pore volumes with the pore diameters in these predetermined ranges appropriately, the adsorption performance of 1,1,1-trichloroethane under the water conducting condition can be improved further more.

The larger the pore volume with the pore diameters of 50 Å to 300 Å, the faster the diffusion and the movement of 1,1,1-trichloroethane in the activated carbon become, which contributes to the improvement of the adsorption performance, so that the pore volume with the pore diameters of 50 Å to 300 Å is preferably 0.02 cm³/g or more, more preferably 0.03 cm³/g or more, and further preferably 0.05 cm³/g or more. An upper limit thereof is not determined particularly, but is preferably 2.0 cm³/g or less, and more preferably 1.0 cm³/g or less.

Similarly, in the light of the improvement of the adsorption performance, the pore volume with the pore diameters of 100 Å to 300 Å is also preferably 0.02 cm³/g or more, more preferably 0.03 cm³/g or more, and further preferably 0.04 cm³/g or more. An upper limit thereof is not determined particularly, but is preferably 2.0 cm³/g or less, and more preferably 1.0 cm³/g or less.

Similarly, in the light of the improvement of the adsorption performance, the pore volume with the pore diameters of 200 Å to 300 Å is also preferably 0.01 cm³/g or more, and more preferably 0.02 cm³/g or more. An upper limit thereof is not determined particularly, but is preferably 2.0 cm³/g or less, and more preferably 1.0 cm³/g or less. In particular, by controlling the pore volume with the above-described pore diameters of 200 Å to 300 Å of the activated carbon which satisfies the equilibrium adsorption amount appropriately, the diffusion rate of 1,1,1-trichloroethane can be further improved, whereby the water conduction amount can be increased.

Moreover, the activated carbon of the present invention preferably has a peak which is higher than that of a log differential pore volume value with the pore diameter of 100 Å in a range of the pore diameters of more than 200 Å and 300 Å or less (hereinafter, also called as the "range of the pore diameters of 200 Å to 300 Å") in a pore diameter distribution diagram (vertical axis: log differential pore volume dV/d log D (cm³/g), horizontal axis: pore diameter D (Å)) obtained by measurement by a nitrogen adsorption method. If having such a high peak of the pore volume value in the range of the pore diameters of 200 Å to 300 Å, the mesopores effectively act on the intake of 1,1,1-trichloroethane into the pores under the water conducting condition, and play an effective role to the introduction of the intaken 1,1,1-trichloroethane into the micropores, so that such mesopores are considered to act on the improvement of the adsorption performance of 1,1,1-trichloroethane under the water conducting condition effectively.

Further, in the pore diameter distribution diagram, where values of the log differential pore volume when the pore diameters are 100 Å, 200 Å and 250 Å are $V_{100}$, $V_{200}$ and $V_{250}$, respectively, these values preferably satisfy relations of $V_{200} > V_{100}$ and $V_{250} > V_{200}$. If $V_{100}$, $V_{200}$ and $V_{250}$ satisfy these relations, the micropores and the mesopores communicate with each other effectively, so that the diffusion rate and the moving speed of 1,1,1-trichloroethane into the inside of the activated carbon under the water conducting condition are increased, thereby improving the water conduction amount as a result.

A BET specific surface area of the activated carbon is not limited particularly, but if it is too small, the sufficient adsorption amount cannot be obtained, and on the other hand, if the BET specific surface area is too large, the balance of the pore volume is not necessarily secured. The BET specific surface area of the activated carbon is preferably 500 cm²/g or more, more preferably 600 cm²/g or more, further preferably 700 cm²/g or more, preferably 3000 cm²/g or less, more preferably 2500 cm²/g or less, and further preferably 2000 cm²/g or less.

The activated carbon of the present invention may satisfy the pore volumes of the respective pore diameters, and a total pore volume $(V)_{total}$, is not limited, but if the total pore volume $(V_{total})$ is too small, the sufficient adsorption performance cannot be secured. Thus, the total pore volume $(V_{total})$ is preferably 0.30 cm³/g or more, more preferably 0.40 cm³/g or more, and further preferably 0.50 cm³/g or more. An upper limit of the total pore volume $(V_{total})$ is not limited particularly, and is preferably 0.80 cm³/g or less, and more preferably 0.70 cm³/g or less.

An average pore diameter of the activated carbon of the present invention is not limited particularly, but in the light of the improvement of the introduction efficiency of 1,1,1-trichloroethane into the inside of the activated carbon, it is preferably 15 Å or more, more preferably 20 Å or more, further preferably 21 Å or more, and still further preferably 22 Å or more. Whereas, an upper limit of the average pore diameter is not limited particularly, but is preferably 40 Å or less, more preferably 35 Å or less, and further preferably 30 Å or less.

The activated carbon of the present invention has the excellent adsorption performance of 1,1,1-trichloroethane, but its adsorbate is not limited to 1,1,1-trichloroethane, and the activated carbon exhibits the excellent adsorption performance also of trihalomethane compounds such as chloroform and the like.

Further, the activated carbon of the present invention is suitably used as activated carbon for removing 1,1,1-trichloroethane under the water conducting condition, and the water conduction amount that can maintain a removal rate of 1,1,1-trichloroethane, which is obtained by a water conduction test conducted in the below-described examples, to be 80% or more is preferably 50 L/g or more, more preferably 60 L/g or more, further preferably 70 L/g or more, and still further preferably 80 L/g or more. The activated carbon of the present invention is useful as, for example, activated carbon for a water purifier.

A method for manufacturing the activated carbon of the present invention is not limited particularly, as long as activated carbon that satisfies the above-described equilibrium adsorption amount and specific pore volume with the pore diameters can be manufactured. Hereinafter, the method for manufacturing the activated carbon of the present invention will be described specifically, but the manufacturing method of the present invention is not limited to below-described manufacturing examples, and can be modified as appropriate, and the thus modified methods are also included in the present invention.

A manufacturing method which can sufficiently secure micropores that influence an adsorption amount of 1,1,1-trichloroethane and can control formation of the mesopores that contribute to the improvement of the diffusion rate of 1,1,1-trichloroethane has not been known so far. As a result of accumulated study of the inventors of the present invention, they have found that, when phenol resin carbide or activated carbon obtained from phenol resin (which is obtained by activating the phenol resin carbide at least once) is subjected to steam activation, it is necessary for the steam activation material (the phenol resin carbide or its activated product) to be loaded with at least one of a calcium compound and a potassium compound (hereinafter, called as the "calcium compound or the like"). When performing the steam activation, if the steam activation material is loaded with the calcium compound or the like, the mesoporous can be developed, while the micropores remain. Incidentally, a timing for loading with the calcium compound or the like is not limited particularly, and it can be loaded at any time until obtaining the steam activation material from the phenol resin, as long as the loading state of the calcium compound can be maintained.

For example, (i) the phenol resin may be loaded with the calcium compound or the like, (ii) the phenol resin carbide may be loaded with the calcium compound or the like, or (iii) the phenol resin which is carbonized and then activated may be loaded with the calcium compound or the like, and in short, such a phenol resin derivative (which means the phenol resin, the phenol resin carbide, the activated product of the phenol resin or the like, and the same shall apply hereafter) is necessary to be loaded with the calcium compound or the like.

Incidentally, as the carbon material to be used for manufacturing the activated carbon of the present invention, in the light of availability and cost of the material, controllability of the relation between the pore diameter and the pore volume and the like, fibrous phenol resin (hereinafter, called as the "phenol resin fiber") is recommended.

As a consequence, the phenol resin derivative is treated sequentially by carbonizing the phenol resin fiber, and subsequently activating the phenol resin fiber carbide at least once, where any one of the activation is steam activation, and the phenol resin derivative is loaded with the calcium compound or the like by the time when performing this one-time steam activation, and is subjected to the steam activation while maintaining the loading state.

Further, in the manufacturing method of the present invention, the phenol resin derivative is necessary to be loaded with the calcium compound or the like before performing the steam activation. Thus, (1) the phenol resin fiber may be loaded with the calcium compound or the like and subsequently carbonized, and then the obtained loaded carbide may be subjected to the steam activation; or (2) the phenol resin fiber may be carbonized and subsequently loaded with the calcium compound or the like, and thereafter, the obtained loaded carbide may be subjected to the steam activation. Alternatively, (3) the phenol resin fiber may be carbonized and subsequently activated, and the obtained activated product of the phenol resin fiber may be loaded with the calcium compound or the like, and then, the loaded product may be subjected to the steam activation. Needless to say, the loading with the calcium compound or the like may be performed plural times, that is, in arbitrary different steps in the manufacturing process. For example, the phenol resin fiber may be loaded with the calcium compound or the like and subsequently carbonized, and thereafter, the thus obtained carbide may be loaded with the calcium compound or the like again. Alternatively, the phenol resin fiber may be carbonized, subsequently loaded with the calcium compound or the like and then activated, and thereafter, the obtained activated product of the phenol resin fiber may be loaded with the calcium compound or the like and subsequently subjected to the steam activation.

The activated carbon obtained by performing the activation treatment to the phenol resin fiber (hereinafter, also called as the "activated product of phenol resin fiber") exhibits a superior pressure loss during the water conduction and has a larger outer surface area than those of granular activated carbon, and can be accordingly in contact with treating aqueous solution with high efficiency so as to increase its water conduction amount. Further, its fibrous form enables a desired shape such as a filter to be molded easily. A fiber length and a fiber diameter of the phenol resin fiber are not limited particularly, and may be determined as appropriate according to its use. For example, an average fiber length thereof is preferably 1 mm to 100 mm, and an average fiber diameter thereof is preferably no more than 200 μM.

Incidentally, the phenol resin fiber may be obtained by processing the phenol resin into the fibrous form by a known method, or may be a commercial product. A method for manufacturing the phenol resin fiber is not limited particularly, and various known manufacturing methods such as an electrostatic spinning method and a blend spinning method can be adopted.

In the present invention, the phenol resin fiber is carbonized before or after being loaded with the calcium compound or the like, and various conditions for the carbonization treatment are not limited particularly. Usually, the phenol resin fiber may be treated by heat under an inert gas atmosphere such as nitrogen, helium and argon at a temperature for a time period as long as the phenol resin fiber is not burnt. The temperature for the carbonization treatment is preferably 500° C. or more, more preferably 550° C. or more, preferably 1200° C. or less, and more preferably 1000° C. or less. In addition, a retention time at the carbonization treatment temperature is preferably 5 minutes to 3 hours. Incidentally, a temperature increasing rate until reaching the carbonization treatment temperature is not limited particularly, and is preferably 1° C./minute to 20° C./minute.

Further, in the present invention, the phenol resin fiber carbide is activated at least once, and for example, the activated product of the phenol resin fiber obtained by performing the activation treatment to the phenol resin fiber carbide may be loaded with the calcium compound or the like, and may be subsequently subjected to the steam activation. Activating conditions for manufacturing the activated product of the phenol resin fiber are not limited particularly, and any activation methods such as steam activation and alkali activation may be adopted. By performing the activation treatment, the BET specific surface area and the total pore volume ($V_{total}$) of the activated carbon can be increased, and the pore volume of the micropores which are effective for improving the equilibrium adsorption amount can also be increased. Thus, in the case of using the activated product of the phenol resin fiber, the activated carbon having a superior equilibrium adsorption amount and water conduction amount can be obtained. For obtaining the favorable BET specific surface area and pore volume ratio, the alkali activation is preferably adopted. Moreover, conditions for the alkali activation treatment are not limited particularly, and known conditions for the alkali activation can be adopted. Further, the activated product of the phenol resin fiber may be subjected to known cleaning treatment and heat treatment as necessary.

In the present invention, the phenol resin fiber, the phenol resin fiber carbide or the activated product of the phenol resin fiber (in other words, the phenol resin derivative) is loaded with the calcium compound or the like. A method for loading the calcium compound or the like is not limited particularly. Examples thereof include: (i) a method of immersing the phenol resin derivative in at least one of calcium compound-containing liquid and potassium compound-containing liquid (hereinafter, called as the "calcium compound-containing liquid or the like"; (ii) a method of spraying the calcium compound-containing liquid or the like to the phenol resin derivative; and (iii) a method of adding at least one of calcium compound-containing powder and potassium compound-containing powder to the phenol resin derivative. Thereafter, the loaded product may be dried as necessary. Further, for enhancing a loading property easily at low cost, the calcium and/or potassium is preferably dissolved in the calcium compound-containing liquid or the like, and as examples of the calcium compound and the potassium compound, calcium carbonate, potassium carbonate, calcium chloride, potassium chloride and the like can be exemplified. Among them, calcium chloride and potassium chloride that have excellent water solubility and are low-cost are preferably used. Moreover, in the above-described loading method, loading conditions, such as use of organic solvent and performing of dry blending, can be selected as appropriate according to properties of the calcium compound or the like.

According to the above-described loading method, the steam activation can be performed while maintaining the loading state of the phenol resin derivative with the calcium compound or the like. In fact, since, if the phenol resin derivative is subjected to wet cleaning such as water washing after being loaded with the calcium compound or the like, the calcium compound or the like is eliminated, it is preferable that the wet cleaning be not carried out after the loading until performing the steam activation, or the phenol resin derivative is loaded with the calcium compound or the like again after the wet cleaning.

Comparing the activated carbon of the present invention, which is obtained by performing the steam activation to the phenol resin derivative in the maintained state of being loaded with the calcium compound or the like, with the conventional activated carbon, which is obtained by performing the steam activation to the phenol resin derivative without being loaded with the calcium compound or the like, these BET specific surface areas, average pore diameters, total pore volumes ($V_{total}$) and the like are equivalent. However, only in the case where the phenol resin derivative in the maintained state of being loaded with the calcium compound or the like is subjected to the steam activation, a state of the activated carbon can be controlled more favorably by the use of the calcium compound or the like, and as a result, the activated carbon having excellent adsorption performance of 1,1,1-trichloroethane can be obtained. That is, if the phenol resin derivative is subjected to the steam activation in the state of being loaded with the calcium compound or the like, mesopores having the predetermined pore diameter, which are not generated in the conventional method, are developed, so that pore diameter distribution of the mesopores which are effective for improving the diffusion rate of 1,1,1-trichloroethane can be obtained. Further, by performing the steam activation treatment while maintaining the state of being loaded with the calcium compound or the like, the pore volume of the micropores can maintain an adsorption volume that is sufficient for 1,1,1-trichloroethane, and a sufficient meso-porosity can be secured. Thus, the activated carbon obtained by the manufacturing method of the present invention has a pore diameter distribution which exhibits not only the superior equilibrium adsorption amount but also the excellent adsorption performance of 1,1,1-trichloroethane under the water conducting condition.

A loaded amount of at least one of calcium and potassium (hereinafter, called as the "calcium or the like") is not limited particularly, and may be adjusted as appropriate according to the activating condition, performing or not performing the cleaning treatment and heat treatment after the activation treatment and the like so as to be able to obtain the desired equilibrium adsorption amount and the predetermined pore volume with the pore diameters. If the loaded amount of the calcium or the like is too small, the predetermined pore volume of the mesopores may not be able to be secured even if performing the steam activation. On the other hand, if the loaded amount of the calcium or the like is too large, the pore volume of the micropores may be decreased significantly, or the mesopores may be developed too much, so that the desired activated carbon cannot be sometimes obtained. Therefore, the calcium or the like is preferably 0.01% by mass or more, more preferably 0.1% by mass or more, preferably 10% by mass or less, and more preferably 5% by mass or less with respect to 100% by mass of a total amount of the phenol resin derivative after being loaded with the calcium or the like.

In the case of loading the phenol resin derivative with the calcium or the like using the calcium compound-containing liquid or the like, it is desirable that the subsequent treatment be performed after removing water by drying treatment or the like as necessary.

After loading the phenol resin derivative with the calcium compound or the like, the loaded product is subjected to the steam activation treatment while maintaining the loading state. As the steam activation, activation treatment is performed by heating a heating furnace until reaching the predetermined temperature and then supplying steam.

Conditions for the steam activation treatment are not limited particularly, as long as the activated carbon of the present invention having the predetermined equilibrium adsorption amount and the predetermined pore volume with the pore diameters can be obtained. For example, the steam activation is preferably performed under an inert gas atmosphere such as nitrogen, argon and helium. Further, a temperature for performing the steam activation (a temperature in the heating furnace) is preferably 400° C. or more, more preferably 450° C. or more, preferably 1500° C. or less, and more preferably 1300° C. or less. A heating period for performing the steam activation is preferably 1 minute or more, more preferably 5 minutes or more, preferably 10 hours or less, and more preferably 5 hours or less.

A total amount of the steam to be supplied during the activation treatment is not also limited particularly. Also, a state of supplying the steam is not limited particularly, and can be, for example, either of: a state of supplying the steam which is not diluted; and a state of diluting the steam with inert gas and supplying the mixed gas. In order to allow an activating reaction to proceed efficiently, it is preferable to adopt the state of diluting the steam with inert gas and supplying the mixed gas. In the case of diluting the steam with inert gas and supplying the mixed gas, partial steam pressure in the mixed gas (total pressure: 101.3 kPa) is preferably 30 kPa or more, and more preferably 40 kPa or more.

(Other Treatment)

The activated carbon obtained by the steam activation may be further subjected to cleaning treatment, heat treatment or the like as necessary. The cleaning treatment is performed to the activated carbon after the steam activation by using known solvent such as water, acid solution and alkaline solution. By cleaning the activated carbon, impurities such as calcium or the like and ash can be removed.

The heat treatment is preferably performed by further heating the activated carbon after the steam activation or the cleaning under an inert gas atmosphere. By treating the activated carbon by heat, residual chlorine and surface functional groups contained in the activated carbon can be removed. Conditions for the heat treatment are not limited particularly, and for example, a heat treating temperature is preferably 400° C. or more and 1000° C. or less, and a retention time is preferably 5 minutes or more and 3 hours or less.

The activated carbon obtained by the manufacturing method of the present invention can exhibit not only the superior equilibrium adsorption amount of 1,1,1-trichloroethane but also the excellent adsorption performance even under the water conducting condition because of its optimized pore structure.

Incidentally, in the present invention, the activation treatment may be performed plural times, but after carrying out the steam activation in the state of loading with the calcium compound or the like, further activation is not preferably performed. If activation is performed after the steam activation, pore diameters may be further increased or the like, so that the activated carbon having the desired equilibrium adsorption amount and the predetermined pore volume with the pore diameters cannot be sometimes obtained.

Further, in the manufacturing method of the present invention, oxidation treatment is not performed to the phenol resin derivative before the loading it with the calcium or the like. The reason for this is because, if such oxidation treatment is performed as disclosed in Patent Document 2, the phenol resin derivative is modified, and even if the phenol resin derivative is loaded with the calcium compound or the like and then subjected to the steam activation treatment, the activated carbon having the desired pore diameter distribution cannot be obtained, whereby the adsorption performance of 1,1,1-trichloroethane cannot be improved.

The present application claims priority to Japanese Patent Application No. 2014-152010 filed on Jul. 25, 2014. The entire contents of the disclosure of Japanese Patent Application No. 2014-152010 filed on Jul. 25, 2014 are incorporated herein by reference.

EXAMPLES

The present invention will be illustrated in further detail with reference to experimental examples below. It should be noted, however, that these examples are never construed to limit the scope of the present invention; and various modifications and changes may be made without departing from the scope and sprit of the present invention described hereinbefore and hereinafter and should be considered to be within the scope of the present invention.

Activated Carbon No. 1

Phenol resin fiber (average fiber diameter: 14 µm, average fiber length: 70 mm) as a carbon material was immersed in calcium chloride ($CaCl_2$) aqueous solution which was retained at a room temperature, and was subsequently dried at 110° C., thereby obtaining phenol resin fiber loaded with the calcium compound (a loaded amount of the calcium with respect to the phenol resin fiber after being loaded with the calcium was 0.5% by mass). Thereafter, while maintaining a state of being loaded with the calcium compound, the phenol resin fiber was subjected to carbonization treatment at 600° C. under a nitrogen atmosphere. After the carbonization treatment, steam activation treatment (partial steam pressure: 70 kPa) was performed by retaining the phenol resin fiber carbide at 900° C. in a heating furnace under a nitrogen atmosphere for 10 minutes, thereby obtaining Activated Carbon No. 1.

Activated Carbon No. 2

Activated Carbon No. 2 was manufactured similarly to Activated Carbon No. 1 except for performing acid cleaning treatment (concentration of hydrochloric acid: 5.25% by mass) after the steam activation and subsequently performing the heat treatment by retaining the phenol resin fiber at 750° C. in a heating furnace under a nitrogen atmosphere for 2 hours.

Activated Carbon Nos. 3 and 4 Activated Carbon Nos. 3 and 4 was manufactured similarly to Activated Carbon No. 1 except for immersing the phenol resin fiber in sodium chloride (NaCl) aqueous solution (No. 3) or potassium chloride (KCl) aqueous solution (No. 4) instead of calcium chloride ($CaCl_2$) aqueous solution, and changing the time period of the steam activation from 10 minutes to 5 minutes.

Activated Carbon No. 5

The phenol resin fiber was subjected to carbonization treatment at 600° C. under a nitrogen atmosphere. After the carbonization treatment, steam activation was performed by retaining the phenol resin fiber carbide at 900° C. in a heating furnace under a nitrogen atmosphere for 10 minutes, thereby obtaining Activated Carbon No. 5.

Activated Carbon No. 6

Potassium hydroxide was added as an alkali activator to phenol resin fiber carbide, which was obtained by performing carbonization treatment to phenol resin fiber at 600° C., so that their mass ratio (the alkali activator/the phenol resin carbide) might be 0.8, and was subsequently mixed with 150 mL of water sufficiently, thereby obtaining a mixture. Thereafter, this mixture was subjected to alkali activation treatment by being heated until reaching 700° C. (temperature increasing rate: 10° C./minute) in nitrogen gas stream (1 L/minute) and being retained for 2 hours. An activated product of the phenol resin fiber obtained by the alkali activation was immersed in calcium chloride ($CaCl_2$) aqueous solution that was retained at a room temperature, and was subsequently dried at 110° C., thereby obtaining an activated product of the phenol resin fiber that was loaded with the calcium compound. Thereafter, while maintaining the loading state of the calcium compound, the activated product of the phenol resin fiber was subjected to steam activation by being retained at 900° C. in a heating furnace under a nitrogen atmosphere for 5 minutes (partial steam pressure: 70 kPa). After the steam activation treatment, acid cleaning treatment and heat treatment were performed similarly to those of Activated Carbon No. 2, thereby producing Activated Carbon No. 6.

Activated Carbon No. 7

The activated product of the phenol resin fiber was subjected to acid cleaning and heat treatment that are similar to those of Activated Carbon No. 2, thereby producing Activated Carbon No. 7.

Activated Carbon No. 8

Activated carbon simulating that of Patent Document 2 was produced. More specifically, Activated Carbon No. 8 was produced similarly to Activated Carbon No. 1 except for using isotropic pitch-based carbon fiber instead of the phenol resin fiber as the carbon material.

Activated Carbon No. 9

Isotropic pitch-based carbon fiber was subjected to carbonization treatment at 600° C. under a nitrogen environment. After the carbonization treatment, steam activation was performed by retaining the carbon fiber carbide at 900° C. in a heating furnace under a nitrogen atmosphere for 10 minutes, thereby obtaining Activated Carbon No. 9.

Activated Carbon No. 10

Activated Carbon No. 10 was produced similarly to Activated Carbon No. 1 except for using anisotropic pitch-based carbon fiber instead of the phenol resin fiber as the carbon material.

Activated Carbon No. 11

Activated Carbon No. 11 was produced similarly to Activated Carbon No. 5 except for using anisotropic pitch-based carbon fiber instead of the phenol resin fiber as the carbon material.

(Measurement Conditions, etc.)

1. Calculation of Loaded Amount of Loading Substance

A loaded amount (% by mass) was calculated from a mass of the loading substance with respect to the phenol resin derivative at the time of loading.

2. Specific Surface Area and Total Pore Volume

After heating 0.2 g of activated carbon at 250° C. under vacuum, an adsorption isotherm was obtained using a nitrogen adsorption apparatus ("ASAP-2400" produced by Micromeritics Instrument Corporation), a specific surface area ($m^2/g$) was calculated by a BET method, and a total pore volume ($V_{total}$: $cm^3/g$) was calculated from a nitrogen adsorption amount at the time when relative pressure $P/P_0$ (P: gas pressure of an adsorbate in adsorption equilibrium, $P_0$: saturated vapor pressure of the adsorbate at an adsorption temperature) was 0.93. The thus obtained specific surface areas will be listed in a column of "Specific Surface Area ($m^2/g$)" in Table 2, and the total pore volumes ($V_{total}$: $cm^3/g$) will be listed in a column of "Total Pore Volume ($V_{total}$: $cm^3/g$)" in Table 2.

3. Pore Volumes of Respective Pore Diameters

The adsorption isotherm was analyzed by the BJH method so as to calculate pore volumes of respective pore diameters in a range of the total pore volume ($V_{total}$). The pore volumes will be listed in columns of "Pore Volume ($cm^3/g$)" in Table 2 according to the pore diameters.

Pore volume with pore diameters of 20 Å or less ($\leq V_{20 Å}$: $cm^3/g$)=total pore volume ($V_{total}$: $cm^3/$ g)−(pore volume with pore diameters of more than 20 Å and 300 Å or less ($V_{20-300 Å}$: $cm^3/g$)) (1)

Pore volume with pore diameters of more than 20 Å and 300 Å or less ($V_{20-300 Å}$: $cm^3/g$)=total pore volume ($V_{total}$: $cm^3/g$)−(pore volume with pore diameters of 20 Å or less ($\leq V_{20 Å}$: $cm^3/g$)) (2)

Pore volume with pore diameters of more than 50 Å and not 300 Å or less ($V_{50-300 Å}$: $cm^3/g$)=total pore volume ($V_{total}$: $cm^3/g$)−(pore volume with pore diameters of 20 Å or less ($\leq V_{20 Å}$: $cm^3/g$)+pore volume with pore diameters of more than 20 Å and 50 Å or less ($V_{20-50 Å}$: $cm^3/g$)) (3)

Pore volume with pore diameters of more than 100 Å and 300 Å or less ($V_{100-300 Å}$: $cm^3/g$)=total pore volume ($V_{total}$: $cm^3/g$)−(pore volume with pore diameters of 20 Å or less ($\leq V_{20 Å}$: $cm^3/$ g)+pore volume with pore diameters of more than 20 Å and 100 Å or less ($V_{20-100 Å}$: $cm^3/g$)) (4)

Pore volume with pore diameters of more than 200 Å and 300 Å or less ($V_{200-300 Å}$: $cm^3/g$)=total pore volume ($V_{total}$: $cm^3/g$)−(pore volume with pore diameters of 20 Å or less ($\leq V_{20 Å}$: $cm^3/$ g)+pore volume with pore diameters of more than 20 Å and 200 Å or less ($V_{20-200 Å}$: $cm^3/g$)) (5)

4. Meso-Porosity

Based on the total pore volume ($V_{total}$: $cm^3/g$) and the pore volume with the pore diameters of more than 20 Å and 300 Å or less ($V_{20-300 Å}$: $cm^3/g$), meso-porosity (%) was calculated. Results will be described in a column of "Meso-Porosity (%)" in Table 2.

5. Pore Volume (dV/d log D)—Pore Diameter Distribution

Based on a pore diameter distribution diagram (vertical axis: log differential pore volume dV/d log D ($cm^3/g$), horizontal axis: pore diameter D (Å)) obtained by measurement by a nitrogen adsorption method, values with pore diameters of 20 Å, 50 Å, 100 Å, 200 Å and 250 Å in the horizontal axis were obtained. Results will be described in a column of "Pore Volume (dV/d log D) Pore Diameter Distribution" in Table 2.

6. Average Pore Diameter

Based on the pore volumes and the specific surface areas in the range of the pore diameters from 10 Å to 300 Å, average pore diameters were calculated by the BJH method from a below formula (6). Results will be described in a column of "Average Pore Diameter (Å)" in Table 2.

Average pore diameter (Å)=(4×pore volume ($cm^3/$ g))/specific surface area ($m^2/g$)×10000 (6)

7. Equilibrium Test

After diluting 0.5 g of 1,1,1-trichloroethane with 50 mL of methanol, the obtained solution was further diluted with methanol by 10 times so as to prepare stock solution. By diluting 5 mL of the stock solution with pure water, aqueous solution of 1,1,1-trichloroethane with a concentration of 5 mg/L was prepared. After putting a stirrer and activated carbon into a brown Erlenmeyer flask with a capacity of 100 mL, the Erlenmeyer flask was filled with the aqueous solution of 1,1,1-trichloroethane and was sealed. Thereafter, the Erlenmeyer flask was placed in a thermostatic oven which was maintained at 20° C., and the aqueous solution was stirred for 14 hours. After 14 hours, the aqueous solution in the Erlenmeyer flask was filtered by a syringe filter. From the thus obtained filtrate, an equilibrium concentration (mg/ L) of the aqueous solution of 1,1,1-trichloroethane was obtained by headspace gas chromatography, and an equilibrium adsorption amount (mg/g) of the aqueous solution of 1,1,1-trichloroethane was obtained by dividing the equilibrium concentration by the mass of the activated carbon so as to draw an adsorption isotherm, by which an equilibrium adsorption amount of 1,1,1-trichloroethane at the equilibrium concentration of 0.3 mg/L was calculated so as to be determined as an adsorption amount of 1,1,1-trichloroethane. Results will be listed in a column of "Equilibrium Adsorption Amount (mg/g)" in the table.

8. Water Conduction Test

A column (diameter: 10 mm) was filled with 0.15 g of activated carbon, and a water conduction test was performed in accordance with JIS S 3201 (a household water purifier testing method in 2010). More specifically, raw water, which was prepared to have a 1,1,1-trichloroethane concentration of 0.3±0.060 mg/L, was allowed to pass through the column at space velocity (SV) of 3000 $h^{-1}$. Quantitative measurement of the 1,1,1-trichloroethane concentrations before and after passing through the column was performed by headspace gas chromatography. Assuming that the 1,1,1-trichloroethane concentration of outflow water of the column was 20% with respect to inflow water thereof at a break point, a water conduction amount of 1,1,1-trichloroethane at the time of reaching the break point (=[total amount of filtered water until reaching break point (L)/mass of activated carbon (g)]) was calculated so as to evaluate filter performance. Incidentally, TurboMatrix HS produced by PerkinElmer Inc. as a headspace, and QP2010 produced by Shimadzu Corporation as a gas chromatograph mass spectrometer were used. Results will be described in a column of "Water Conduction Amount (L/g)" in Table 2. In addition, relation between the water conduction amount and a removal rate of 1,1,1-trichloroethane will be illustrated in FIG. 1.

TABLE 1

| No. | Carbon Material | Loading Substance | Loaded Amount (% by mass) | Activating Time Period (min) | Acid Cleaning | Heat Treatment |
|---|---|---|---|---|---|---|
| 1 | Phenol Resin Fiber | CaCl$_2$ | 0.5 | 10 | Not Performed | Not Performed |
| 2 | | | | | Performed | Performed |
| 3 | | NaCl | 0.5 | 5 | Not Performed | Not Performed |
| 4 | | KCl | 0.5 | 5 | Not Performed | Not Performed |
| 5 | | — | — | 10 | Not Performed | Not Performed |
| 6 | Activated Product of Phenol | CaCl$_2$ | 0.5 | 5 | Performed | Performed |
| 7 | Resin Fiber | — | — | — | Performed | Performed |
| 8 | Isotropic Pitch-based Fiber | CaCl$_2$ | 0.5 | 10 | Not Performed | Not Performed |
| 9 | | — | — | 10 | Not Performed | Not Performed |
| 10 | Anisotropic Pitch-based Fiber | CaCl$_2$ | 0.5 | 10 | Not Performed | Not Performed |
| 11 | | — | — | 10 | Not Performed | Not Performed |

TABLE 2

| No. | Specific Surface Area (m$^2$/g) | Total Pore Volume ($V_{total}$ cm$^3$/g) | Pore Volume (cm$^3$/g)* | | | | | Meso-porosity (%) | Pore Volume (dV/dlogD) Pore Diameter Distribution | | | | | Average Pore Diameter (Å) | Equilibrium Adsorption Amount (mg/g) | Water Conduction Amount (L/g) |
|---|---|---|---|---|---|---|---|---|---|---|---|---|---|---|---|---|
| | | | -20 Å | 20-300 Å | 50-300 Å | 100-300 Å | 200-300 Å | | 20 Å | 50 Å | 100 Å | 200 Å | 250 Å | | | |
| 1 | 905 | 0.49 | 0.37 | 0.12 | 0.08 | 0.06 | 0.03 | 23.5 | 0.13 | 0.07 | 0.09 | 0.14 | 0.16 | 24.4 | 41 | 63 |
| 2 | 967 | 0.52 | 0.41 | 0.11 | 0.07 | 0.05 | 0.02 | 22.0 | 0.15 | 0.08 | 0.09 | 0.11 | 0.12 | 21.9 | 38 | 86 |
| 3 | 951 | 0.44 | 0.41 | 0.03 | 0.01 | 0.01 | 0.00 | 6.6 | 0.10 | 0.02 | 0.01 | 0.02 | 0.02 | 15.0 | 53 | 23 |
| 4 | 937 | 0.45 | 0.40 | 0.05 | 0.03 | 0.02 | 0.01 | 10.3 | 0.10 | 0.03 | 0.03 | 0.04 | 0.06 | 17.0 | 52 | 66 |
| 5 | 1058 | 0.49 | 0.46 | 0.03 | 0.01 | 0.01 | 0.00 | 5.9 | 0.12 | 0.01 | 0.01 | 0.01 | 0.01 | 14.4 | 40 | 21 |
| 6 | 1120 | 0.58 | 0.46 | 0.12 | 0.07 | 0.04 | 0.02 | 19.8 | 0.18 | 0.08 | 0.08 | 0.09 | 0.10 | 20.2 | 56 | 134 |
| 7 | 1076 | 0.49 | 0.47 | 0.02 | 0.01 | 0.00 | 0.00 | 3.9 | 0.10 | 0.01 | 0.01 | 0.01 | 0.01 | 14.2 | 53 | 11 |
| 8 | 656 | 0.35 | 0.26 | 0.09 | 0.03 | 0.01 | 0.01 | 25.7 | 0.16 | 0.11 | 0.04 | 0.02 | 0.02 | 19.5 | 9 | 18 |
| 9 | 755 | 0.35 | 0.33 | 0.02 | 0.01 | 0.00 | 0.00 | 5.8 | 0.08 | 0.01 | 0.01 | 0.01 | 0.01 | 14.5 | 19 | 13 |
| 10 | 88 | 0.06 | 0.03 | 0.03 | 0.02 | 0.01 | 0.01 | 45.7 | 0.04 | 0.02 | 0.02 | 0.03 | 0.03 | 23.8 | 4 | 1 |
| 11 | 146 | 0.08 | 0.05 | 0.03 | 0.02 | 0.01 | 0.00 | 34.7 | 0.05 | 0.02 | 0.02 | 0.02 | 0.02 | 20.8 | 5 | 2 |

*[-20 Å] denotes pore diameters of 20 Å or less, [20-300 Å] denotes pore diameters of more than 20 Å and 300 Å or less, [50-300 Å] denotes pore diameters of more than 50 Å and 300 Å or less, [100-300 Å] denotes pore diameters of more than 100 Å and 300 Å or less, and [200-300 Å] denotes pore diameters of more than 200 Å and 300 Å or less.

As shown in Tables 1 and 2, Activated Carbon Nos. 1, 2, 4 and 6 which satisfied the requirements of the present invention exhibited good results in both of the equilibrium adsorption amounts and the water conduction amounts. Further, Activated Carbon Nos. 1, 2, 4 and 6 of the present invention had higher peaks than the log differential pore volume value with the pore diameter of 100 Å in the range of the pore diameters of 200 Å to 300 Å, as shown in FIGS. 2, 3, 4, 6 and 8. On the other hand, Activated Carbon Nos. 3, 5 and 7 to 11 which did not satisfy the requirements of the present invention exhibited the less water conduction amounts. Moreover, as shown in FIG. 1, for example, in the case of using the calcium compound or the potassium compound as the loading substance (Activated Carbon Nos. 1 and 4), the removal rates of 1,1,1-trichloroethane under the water conducting condition were much higher than those in the case of using the sodium compound (No. 3) and the case of loading with nothing (No. 5).

Activated Carbon No. 3 was the example of using sodium as the loading substance. Activated Carbon No. 3 had the sufficient micropore volume, but its pore volume with the pore diameters of 20 Å to 300 Å was small, whereby its water conduction amount was small. Further, as shown in FIG. 5, Activated Carbon No. 3 did not exhibit any peak that was higher than the log differential pore volume value with the pore diameter of 100 Å in the range of the pore diameters of 200 Å to 300 Å.

Activated Carbon Nos. 5 and 7 were the examples of using no loading substance. Each of Activated Carbon Nos. 5 and 7 had the sufficient micropore volume, but their pore volume with the pore diameters of 20 Å to 300 Å was small, whereby their water conduction amounts were small. Further, as shown in FIGS. 2 and 7, Activated Carbon No. 5 did not exhibit any peak that was higher than the log differential pore volume value with the pore diameter of 100 Å in the range of the pore diameters of 200 Å to 300 Å.

Activated Carbon No. 8 was the example in which the isotropic pitch-based fiber was loaded with the calcium compound as the loading substance, and Activated Carbon No. 9 was the example where the isotropic pitch-based fiber was not loaded with any loading substance. Since each of Activated Carbon Nos. 8 and 9 had the small micropore volume and the small pore volume with the pore diameters of 20 Å to 300 Å, their equilibrium adsorption amounts and water conduction amounts were small. Further, as shown in FIG. 9, Activated Carbon No. 8 which was loaded with the calcium compound had the larger pore volume with the pore diameters of less than 100 Å than that of Activated Carbon No. 9 which was not loaded with Ca, but none of Activated Carbon Nos. 8 and 9 exhibited a peak that was higher than the log differential pore volume value with the pore diameter of 100 Å in the range of the pore diameters of 200 Å to 300 Å.

Activated Carbon No. 10 was the example in which the anisotropic pitch-based fiber was loaded with the calcium compound as the loading substance, and Activated Carbon No. 11 was the example where the anisotropic pitch-based fiber was not loaded with any loading substance. Since Activated Carbon Nos. 10 and 11 had almost no pore formed by the steam activation, and had the small specific surface areas, the small micropore volume and the small pore volume with the pore diameters of 20 Å to 300 Å, their equilibrium adsorption amounts and water conduction amounts were poor. Further, as shown in FIG. 10, none of Activated Carbon Nos. 10 and 11 could have sufficient mesopores formed in all of the regions, and exhibited any peak that was higher than the log differential pore volume value with the pore diameter of 100 Å in the range of the pore diameters of 200 Å to 300 Å.

The invention claimed is:

1. An activated carbon with excellent adsorption performance, wherein:
    an equilibrium adsorption amount of 1,1,1-trichloroethane of the activated carbon is 20 mg/g or more;
    a pore volume of pores having a diameter of more than 20 Å and 300 Å or less in the activated carbon is 0.04 cm$^3$/g or more; and
    a pore volume of pores having a diameter of more than 200 Å and 300 Å or less in the activated carbon is 0.01 cm$^3$/g or more.

2. The activated carbon according to claim 1,
    further having a peak higher than that of a log differential pore volume value of pores having a diameter of 100 Å in a range of the pore diameters of more than 200 Å and 300 Å or less in a pore diameter distribution diagram,
    wherein in the pore diameter distribution diagram, a vertical axis is the log differential pore volume dV/d log D in cm$^3$/g and a horizontal axis is the pore diameter D in Å.

3. The activated carbon according to claim 1,
    wherein a pore volume of pores having a diameter of more than 50 Å and 300 Å or less is 0.02 cm$^3$/g or more.

4. The activated carbon according to claim 1,
    wherein a pore volume of pores having a diameter of more than 100 Å and 300 Å or less is 0.02 cm$^3$/g or more.

5. The activated carbon according to claim 2,
    wherein the activated carbon satisfies the following relationship: $V_{200} > V_{100}$, and $V_{250} > V_{200}$
    wherein $V_{100}$, $V_{200}$ and $V_{250}$ are a log differential pore volume value of pores having a diameter of 100 Å, 200 Å and 250 Å, respectively, in a range of the pore diameters of more than 200 Å and 300 Å or less in the pore diameter distribution diagram.

* * * * *